United States Patent [19]

Wu et al.

[11] Patent Number: 5,789,642
[45] Date of Patent: Aug. 4, 1998

[54] HYDROCARBON CONVERSION CATALYST COMPOSITION AND PROCESSES THEREFOR AND THEREWITH

[75] Inventors: An-hsiang Wu, Bartlesville; Charles A. Drake, Nowata, both of Okla.

[73] Assignee: Phillips Petroleum Company, Bartlesville, Okla.

[21] Appl. No.: 764,435

[22] Filed: Dec. 12, 1996

[51] Int. Cl.$^6$ ................................................. C07C 4/12
[52] U.S. Cl. ........................... 585/489; 585/488; 585/486
[58] Field of Search .................... 585/483, 486, 585/487, 488, 489

[56] References Cited

U.S. PATENT DOCUMENTS

| | | | |
|---|---|---|---|
| 4,440,631 | 4/1984 | Togari et al. | 208/112 |
| 5,004,854 | 4/1991 | Yan | 585/489 |
| 5,030,787 | 7/1991 | Absil et al. | 585/475 |
| 5,409,595 | 4/1995 | Harandi | 208/60 |

OTHER PUBLICATIONS

Preparation of Supported–Catalysts by Equilibrium Deposition–Filtration; Scientific Bases for the Preparation of Heterogeneous Catalyst; Poncelet et al., 1995.

*Primary Examiner*—Glenn Caldarola
*Assistant Examiner*—Thuan D. Dang
*Attorney, Agent, or Firm*—Lucas K. Shay

[57] ABSTRACT

A catalyst composition and a process for hydrodealkylating a $C_9+$ aromatic compound to a $C_6$ to $C_8$ aromatic hydrocarbon are disclosed. The composition comprises an alumina, molybdenum oxide, and zinc oxide. The process comprises contacting a fluid which comprises a $C_9+$ aromatic compound with the catalyst composition under a condition sufficient to effect the conversion of a $C_9+$ aromatic compound to a $C_6$ to $C_8$ aromatic hydrocarbon. Also disclosed is a process for producing the composition which comprises: (1) contacting an alumina, which can be optionally calcined before being contacted, with a molybdenum compound and zinc compound in a liquid medium under a condition sufficient to incorporate the molybdenum compound and zinc compound into the alumina to form a modified alumina wherein the volume of the liquid medium is larger than the bulk volume of alumina; (2) removing the excess liquid medium; (3) drying the modified alumina; and (4) calcining the modified alumina to a Mo/Zn-promoted alumina under a condition sufficient to effect the conversion of the molybdenum compound and zinc compound to corresponding oxides.

22 Claims, No Drawings

5,789,642

HYDROCARBON CONVERSION CATALYST COMPOSITION AND PROCESSES THEREFOR AND THEREWITH

FIELD OF THE INVENTION

This invention relates to a catalyst composition useful for converting a $C_9+$ aromatic compound to a $C_6$ to $C_8$ aromatic hydrocarbon, a process for producing the composition, and a process for using the composition in a hydrodealkylation process.

BACKGROUND OF THE INVENTION

It is well known to those skilled in the art that aromatic hydrocarbons are a class of very important industrial chemicals which find a variety of uses in petrochemical industry. Recent efforts to convert gasoline to more valuable petrochemical products have therefore focused on the aromatization of gasoline to aromatic hydrocarbons by catalytic cracking in the presence of a catalyst. The aromatic hydrocarbons produced by the aromatization process include $C_6$ to $C_8$ hydrocarbons such as benzene, toluene and xylenes (hereinafter collectively referred to as BTX) which can be useful feedstocks for producing various organic compounds and polymers. However, heavier, less useful aromatic compounds are also produced during the aromatization process. It is, therefore, highly desirable to convert these compounds to the more useful BTX.

Though a metal oxide-promoted alumina such as $Cr/Al_2O_3$ has been used as catalyst in a hydrodealkylation process, the conversion of a $C_9+$ aromatic compound and the selectivity to BTX are generally not as high as one skilled in the art would desire. One possibility for the low selectivity is that the metal oxide is not uniformly dispersed on the alumina support thereby limiting the total surface area of the catalyst. Therefore, there is an ever-increasing need to develop an improved catalyst and a process for converting these heavier and less useful aromatic compounds to the more valuable BTX hydrocarbons (hereinafter referred to as hydrodealkylation process). Such development would also be a significant contribution to the art and to the economy.

SUMMARY OF THE INVENTION

An object of this invention is to provide a catalyst composition which can be used to convert a $C_9+$ aromatic compound to a $C_6$ to $C_8$ aromatic hydrocarbon. Also an object of this invention is to provide a process for producing the catalyst composition. Another object of this invention is to provide a process which can employ the catalyst composition to convert $C_9+$ aromatic compounds to $C_6$ to $C_8$ aromatic compounds. An advantage of the catalyst composition is that it exhibits high hydrodealkylation activity, satisfactory yield of xylenes and BTX, and good stability. Other objects and advantages will becomes more apparent as this invention is more fully disclosed hereinbelow.

According to a first embodiment of the present invention, a composition which can be used as a catalyst for converting a $C_9+$ aromatic compound to a $C_6$ to $C_8$ aromatic hydrocarbon is provided. The composition is a molybdenum- and zinc-promoted alumina.

According to a second embodiment of the invention, a process for producing a composition which can be used as catalyst in a hydrodealkylation process is provided. The process comprises, consists essentially of, or consists of: (1) contacting an alumina, which can be optionally calcined before being contacted, with both a molylbdenum-containing compound and a zinc-containing compound in a liquid medium under a condition sufficient to incorporate the molybdenum-containing compound and zinc-containing compound into the alumina to form a modified alumina wherein the volume of the liquid medium is larger than the bulk volume of alumina; (2) removing the excess liquid medium containing the molybdenum-containing and zinc-containing compound; (3) drying the modified alumina; and (4) calcining the modified alumina to a Mo/Zn-promoted alumina under a condition sufficient to effect the conversion of the molybdenum-containing compound and zinc-containing compound to corresponding molybdenum oxide and zinc oxide.

According to a third embodiment of the present invention, a process which can be used for converting a $C_9+$ aromatic compound to a $C_6$ to $C_8$ aromatic compound is provided which comprises, consists essentially of, or consists of, contacting a fluid which comprises a $C_9+$ aromatic compound, optionally in the presence of an inert fluid, with a catalyst composition which can be prepared by the process disclosed above in the second embodiment of the invention under a condition effective to convert a $C_9+$ aromatic compound to an aromatic hydrocarbon containing 6 to 8 carbon atoms per molecule.

DETAILED DESCRIPTION OF THE INVENTION

According to the first embodiment of the invention, a composition which can be used as catalyst in a hydrodealkylation process for converting a $C_9+$ aromatic compound to a $C_6$ to $C_8$ aromatic hydrocarbon is provided. The composition can comprise, consist essentially of, or consist of, a molybdenum- and zinc-promoted alumina wherein the molybdenum and zinc are each present in the composition in a BTX selectivity-improving amount to improve the selectivity to BTX when the composition is used in a hydrodealkylation process.

According to the first embodiment of the invention, the weight ratio of elemental molybdenum or zinc to the alumina can be any ratio so long as the ratio can improve the BTX selectivity during a hydrodealkylation process for converting of a $C_9+$ aromatic compound to a $C_6$ to $C_8$ aromatic hydrocarbon. Generally, the ratio can be in the range of from about 0.0001:1 to about 1:1, preferably about 0.0005:1 to about 1:1, more preferably about 0.001:1 to about 0.8:1 and most preferably from 0.005:1 to 0.5:1 for an effective dehydroalkylation conversion. Alternatively, molybdenum or zinc can be present in the catalyst composition in the range of from about 0.001 to about 50, preferably about 0.005 to about 50, more preferably about 0.1 to about 45, and most preferably 0.01 to 33 grams per 100 grams of the catalyst composition.

The alumina can be $\alpha$-alumina, $\beta$-alumina, $\gamma$-alumina, $\eta$-alumina, $\delta$-alumina, or combinations of any two or more thereof. The presently preferred alumina is a $\gamma$-alumina having a surface area in the range of from about 40 to about 300 $m^2/g$, a total pore volume in the range of from about 0.1 to about 1 ml/g.

Any methods known to one skilled in the art for incorporating both molybdenum- and zinc-containing compounds or a portion thereof into an alumina such as, for example, impregnation or extrusion can be employed for producing the composition of the present invention. However, it is presently preferred the composition be produced by the process disclosed in the second embodiment of the invention.

According to the second embodiment of the present invention, the alumina can be α-alumina, β-alumina, γ-alumina, η-alumina, δ-alumina, or combinations of any two or more thereof. The presently preferred alumina is γ-alumina having a surface area in the range of from about 40 to about 300 m²/g, a total pore volume in the range of from about 0.1 to about 1 ml/g. These aluminas are commercially available.

An alumina is generally first treated with aqueous solutions of a molybdenum-containing compound and a zinc-containing compound. An alumina can be optionally calcined before it is used in the second embodiment of the invention to remove any possible contaminant(s) in the alumina. The condition for calcining an alumina can be any condition known to one skilled in the art. The calcining can also be carried out under the condition disclosed hereinbelow.

According to the present invention, any molybdenum-containing or zinc-containing compound which, when incorporated into an alumina, can effect the improvement of selectivity to BTX in a hydrodealkylation process can be employed. Examples of such compounds include, but are not limited to, molybdenum(II) acetate, ammonium molybdate, ammonium dimolybdate, ammonium heptamolybdate, ammonium phosphomolybdate, molybdenum(III) bromide, molybdenum(II) chloride, molybdenum(IV) chloride, molybdenum(V) chloride, molybdenum hexacarbonyl, molybdenum(V) sulfide, sodium molybdate, potassium molybdate, molybdenum oxychloride, molybdenum fluoride, molybdenum(VI) tetrachloride oxide, ammonium tetrathiomolybdate, zinc acetate, zinc acetylacetonate, zinc arsenide, zinc bromide, zinc carbonate hydroxide, zinc chloride, zinc fluoride, zinc hydroxide, zinc iodide, zinc nitrate, zinc stearate, and combinations of any two or more thereof. The presently preferred molybdenum-containing compound is an ammonium or alkali metal heptamolybdate for it is inexpensive and readily available. The presently preferred zinc-containing compound is zinc nitrate, again, for it is readily available.

Generally, in the first step of the process of the second embodiment of the invention, an alumina can be combined with a molybdenum-containing compound and a zinc-containing compound in any suitable weight ratios which would result in the formation of a molybdenum- and zinc-promoted alumina disclosed in the first embodiment of the invention. Preferably the combining of a molybdenum-containing compound and alumina be carried out simultaneously or contemporaneously with the combining of a zinc-containing compound with the alumina. Such combination is carried out in a suitable liquid medium, preferably an aqueous medium, to form an equilibrium alumina-molybdenum-zinc mixture.

It is presently preferred that both the molybdenum-containing compound and zinc-containing compound are each present in the mixture in excess to the quantity that can be fully absorbed by an alumina. Therefore, the volume of the aqueous solution containing both molybdenum-containing and zinc-containing compound is greater than the total or bulk volume of the alumina. Furthermore, the weight ratio of either molybdenum-containing or zinc-containing compound to alumina can be in the range of from about 0.001:1 to about 100:1, preferably about 0.01:1 to about 10:1, and most preferably 0.1:1 to 5:1. The combining of an alumina and the molybdenum-containing compound and zinc-containing compound can be carried out at any temperature. Generally, the temperature can be in the range of from about 25° C. to about 250° C., preferably about 40° C. to about 250° C., and most preferably 50° C. to 150° C. under any pressure, preferably atmospheric pressure, for any length so long as the molybdenum-containing compound, and zinc-containing compound and the alumina are well mixed, generally about 1 minute to about 250 hours, preferably about 1 hour to about 150 hours.

Upon completion of incorporating the molybdenum-containing compound and zinc-containing compound into an alumina, a modified alumina is formed. In the next step of the process, the excess solution containing the molybdenum-containing and zinc-containing compounds is removed. It is presently preferred that the modified alumina is not washed. The removal of the excess solution can be carried out by any methods known to one skilled in the art. Examples of suitable removal methods include filtration, decantation, centrifugation, or combinations of any two or more thereof.

Thereafter, the modified alumina can be dried under any conditions known to one skilled in the art such as, for example, air drying at any temperature. Air drying can be carried out at a temperature for about 25° C. to about 150° C. for about 1 minute to about 30 hours under any pressure such as atmospheric pressure. There is generally no washing of the modified alumina before drying.

In the next step, the modified alumina is subject to calcination under a condition that can include a temperature in the range of from about 300° C. to about 1000° C., preferably about 350° C. to about 750° C., and most preferably 400° C. to 650° C. under a pressure in the range of from about 1 to about 10, preferably about 1 atmospheres for a period in the range of from about 1 to about 30, preferably about 1 to about 20, and most preferably 1 to 15 hours. Upon calcination, a molybdenum (oxide)- and zinc (oxide)-promoted alumina (hereinafter referred to as Mo-Zn/Al₂O₃) is formed.

The modified alumina can also be treated with a steam under a suitable condition sufficient to effect the conversion of the molybdenum-containing compound and zinc-containing compound, which have been incorporated into the alumina, to their corresponding oxide form. The modified alumina can be air dried as disclosed above to remove most moisture content before being steam-treated. The air-dried modified alumina can then be treated with a steam. Generally the steam temperature can be in the range of from about 120° C. to about 1500° C., preferably about 200° C. to about 1200° C., and most preferably 250° C. to 1000° C. The treatment period can be as short as 5 minutes to as long as about 30 hours so long as it is sufficient to convert the molybdenum-containing compound and zinc-containing compound to their oxide form. The treatment can be carried out under a pressure in the range of from about atmospheric pressure to about 2,000, preferably to about 1,500, and most preferably to 1000 psig. The molybdenum- and zinc-promoted alumina, i.e., the calcined product (Mo-Zn/Al₂O₃) disclosed above, can also be steam-treated to improve catalytic activity, or catalyst selectivity, or both.

The composition of the invention thus prepared then can be, if desired, pretreated with a reducing agent before being used in a hydrodealkylation process. The presently preferred reducing agent is a hydrogen-containing fluid which comprises molecular hydrogen ($H_2$) in the range of from 1 to about 100, preferably about 5 to about 100, and most preferably 10 to 100 volume %. The reduction can be carried out at a temperature, in the range of from about 250° C. to about 800° C. for about 0.1 to about 10 hours preferably about 300° C. to about 700° C. for about 0.5 to about 7 hours, and most preferably 350° C. to 650° C. for 1 to 5 hours.

According to the third embodiment of the present invention, a process useful for converting a $C_9+$ aromatic compound to a $C_6$ to $C_8$ aromatic hydrocarbon comprises, consists essentially of, or consists of contacting a fluid stream comprising a $C_9+$ aromatic compound and, optionally, in the presence of an inert fluid such as, for example, hydrogen-containing fluid, with a catalyst composition under a condition sufficient to effect the conversion of a $C_9+$ aromatic compound to a $C_6$ to $C_8$ aromatic hydrocarbon. The inert fluid can be hydrogen, nitrogen, helium, argon, carbon dioxide, neon, steam, and combinations of any two or more thereof. The presently preferred inert fluid is a hydrogen-containing fluid. The inert fluid can also be fed separately into contact with a $C_9+$ aromatic compound and a catalyst. The catalyst composition can be the same as that disclosed in the first embodiment of the invention.

The term "fluid" is used herein to denote gas, liquid, vapor, or combinations of two or more thereof. The term "$C_9+$ aromatic compound" is referred to, unless otherwise indicated, as a substituted aromatic compound containing at least 9 carbon atoms per molecule. Preferably the substituted aromatic compound has the formula of $R_qAr$ wherein each R is a hydrocarbyl radical having 1 to about 15 carbon atoms and is independently selected from the group consisting of alkyl radicals, aryl radicals, alkaryl radicals, aralkyl radicals, alkenyl radicals, and combinations of any two or more thereof, q is a whole number from 1 to 5, and Ar is an aryl, preferably a phenyl, group. More preferably R is an alkyl radical having 1 to about 10 carbon atoms and the aromatic compound has 9 to about 16 carbon atoms per molecule. Most preferably the aromatic compound contains 9 to 12 carbon atoms per molecule.

Any fluid which contains a $C_9$ + aromatic compound as disclosed above can be used as the feed for the process of this invention. The origin of this fluid feed is not critical. However, a preferred fluid feed is a $C_9+$ aromatic compound derived from the heavies fraction of a product from a paraffin, in particular gasoline, aromatization reaction. Generally, this heavies fraction contains primarily trimethylbenzenes such as 1,2,3-trimethylbenzene, 1,2,4-trimethylbenzene, and 1,3,5-trimethylbenzene and tetramethylbenzenes such as 1,2,3,4-tetramethylbenzene, 1,2,3,5-tetramethylbenzene and 1,2,4,5-tetramethylbenzene. Additionally, n-propylbenzene, 3-ethyltoluene, 4-ethyltoluene, 3-n-propyltoluene, 4-n-propyltoluene, and 1,3-diethylbenzene can also be present in the fluid. Benzene, toluene, ethylbenzene, xylenes, and the like are generally substantially absent from the fluid, i.e., the amount of each of these aromatic hydrocarbons is less than about 0.1 weight %. Thus, there is no significant alkylation of these lower aromatic hydrocarbons by the $C_9+$ aromatic compound, i.e., no significant transalkylation occurs as a side-reaction in the process of this invention.

Any hydrogen-containing fluid which comprises, consists essentially of, or consists of, molecular hydrogen ($H_2$) can be used in the process of this invention. This hydrogen-containing fluid can therefore contain $H_2$ in the range of from about 1 to about 100, preferably about 5 to about 100, and most preferably 10 to 100 volume %. If the $H_2$ content in the fluid is less than 100%, the remainder of the fluid may be any inert gas such as, for example, $N_2$, He, Ne, Ar, steam, or combinations of any two or more thereof, or any other fluid which does not significantly affect the process or the catalyst composition used therein.

The contacting of a fluid containing a $C_9+$ aromatic compound, in the presence or absence of a hydrogen-containing fluid, with a catalyst composition can be carried out in any technically suitable manner, in batch, semicontinuous, or continuous process under a condition effective to convert a $C_9+$ aromatic compound to a $C_6$ to $C_8$ aromatic hydrocarbon. Generally, a fluid containing a $C_9+$ aromatic compound, preferably being in the vaporized state, and a hydrogen-containing fluid are introduced into a fixed catalyst bed, or a moving catalyst bed, or a fluidized catalyst bed, or combinations of any two or more thereof by any means known to one skilled in the art such as, for example, pressure, meter pump, and other similar means. The condition can include an hourly space velocity (HSV) of the $C_9+$ aromatic compound fluid stream in the range of about 0.01 to about 100, preferably about 0.05 to about 50, and most preferably 0.1 to 30 g feed/g catalyst/hour. The hydrogen-containing fluid hourly space velocity generally is in the range of about 1 to about 10,000, preferably about 5 to about 7,000, and most preferably 10 to 5,000 $ft^3$ $H_2/ft^3$ catalyst/hour. The preferred molar ratio of $H_2$ to the $C_9+$ aromatic compound can be in the range of from about 0.01:1 to about 20:1, preferably about 0.1:1 to about 10:1, and most preferably 0.5:1 to 5:1. Generally, the pressure can be in the range of from about 30 to about 1000 psig, preferably about 50 to about 750 psig, and most preferably 200 to 600 psig, and the temperature is about 250° to about 1,000° C., preferably about 350° to about 800° C., and most preferably 400° C. to 650° C.

The process effluent generally contains a heavies fraction of unconverted $C_9+$ aromatics and other heavy ($C_9+$) aromatic compounds which may have been formed by side-reactions (such as isomerization); a lights fraction of alkanes, mainly methane, ethane, propane, n-butane, isobutane, and minor amounts (about 0.1 to about 5 weight %) of $C_5$ and $C_6$ alkanes such as, for example, isopentane and n-pentane; and a BTX aromatic hydrocarbons fraction (benzene, toluene, ortho-xylene, meta-xylene and para-xylene). Generally, the effluent can be separated into these principal fractions by fractionation distillation which is well known to one skilled in the art. The heavies fraction can be recycled to a hydrodealkylation reactor described above, the lights fraction can be used as fuel gas or as a feed for other reactions such as, for example, in a thermal cracking process to produce ethylene and propylene, and the BTX fraction can be further separated into individual $C_6$ to $C_8$ aromatic hydrocarbon fractions. Alternatively, the BTX fraction can undergo one or more reactions either before or after separation to individual $C_6$ to $C_8$ hydrocarbons so as to increase the content of the most desired BTX aromatic hydrocarbon. Suitable examples of such subsequent $C_6$ to $C_8$ aromatic hydrocarbon conversions are disproportionation of toluene (to form benzene and xylenes), transalkylation of benzene and xylenes (to form toluene), and isomerization of meta-xylene and/or ortho-xylene to para-xylene.

After the catalyst composition has been deactivated by, for example, coke deposition or feed poisons, to an extent that the feed conversion and/or the selectivity to the most valuable $C_6$ to $C_8$ aromatic product (generally xylenes) have become unsatisfactory, the catalyst composition can be reactivated by any means known to one skilled in the art such as, for example, calcining in air to burn off deposited coke and other carbonaceous materials, such as oligomers or polymers, preferably at a temperature of about 400° to about 650° C., followed by a treatment with a reducing agent such as, for example, with hydrogen gas at a temperature of about 400° to about 600° C. The optimal time periods of the calcining and treatment with a reducing agent depend generally on the types and amounts of deactivating deposits on the catalyst composition and on the calcination and reduction temperatures. These optimal time periods can easily be determined by those possessing ordinary skills in the art and are omitted herein for the interest of brevity.

The following examples are presented to further illustrate this invention and are not to be construed as unduly limiting the scope of the present invention. The examples illustrate the preparation of catalyst compositions of the invention and the use of the composition in a hydrodealkylation process.

A γ-alumina obtained as 1/16 inch extrudates from Criterion Catalyst Company L.P. (Michigan City, Ind.) was used. First, 100 g of the alumina was calcined in air at 525° C. for 3 hours to remove any contaminants. A portion of the alumina (10 g) was well mixed at 25° C. with 2.10 g of zinc nitrate ($Zn(NO_3)_2 \cdot 6H_2O$) containing 70 mmoles of zinc nitrate, 1.24 g of ammonium heptamolybdate (($NH)_6Mo_7O_{24} \cdot 4H_2O$) containing 70 mmoles of ammonium molybdate, and 17.66 g of water to from a mixture. The resulting mixture in a thick wall tube was sealed and heated at 80° C. for 114 hours to form a modified alumina. Thereafter, the excess solution containing zinc nitrate and ammonium heptamolybdate was removed by filtration. After drying in air at room temperature (25° C.) for about 4 hours, the dried, modified alumina was calcined at 525° C. for 4 hours in a muffle furnace (air) to produce 10.73 g of calcined molybdenum oxide- and zinc oxide-promoted alumina or Mo-Zn/$Al_2O_3$ containing 3.00 weight % of zinc and 4.20 weight % molybdenum (Invention Catalyst A). The molybdenum, zinc, and aluminum content was determined by X-ray fluorescence spectrometry (XRF) employing a Siemens MRS 400 multi-channel spectrometer.

Secondly, 12.11 g of the calcined γ-alumina was well mixed with 6.65 g of a 19.555 weight % ammonium heptamolybdate (($NH_4)_6Mo_7O_{24} \cdot 4H_2O$) solution under incipient wetness (conventional impregnation condition) to impregnate all ammonium heptamolybdate onto the alumina, dried as above, and followed by calcining at 538° C. for 6 hours in air to produce 12.19 g of molybdenum oxide-promoted alumina (Control Catalyst B) containing 5.929 weight % of molybdenum by calculation.

Thirdly, 10 g of the calcined γ-alumina was well mixed with 5.27 g of a solution containing 0.53 g of $Zn(NO_3)_2 \cdot 6H_2O$, 0.32 g of $(NH_4)_6Mo_7O_{24} \cdot 6H_2O$, and 4.42 g $H_2O$ in a jar at 25° C. followed by air drying at 25° C. for 16 hours and, thereafter, following transferring to a U-tube, the content was steamed at 650° C. for 6 hours to produce 9.70 g of a molybdenum oxide- and zinc-oxide promoted alumina containing 1.20 weight % molybdenum and 1.10 zinc weight % by XRF described above.

These catalysts were then employed, according to the third embodiment of the invention, in a hydrodealkylation process for converting a $C_9+$ aromatic compound to BTX. The liquid feed in the hydrodealkylation runs was heavy $C_9+$ aromatic compounds obtained in a gasoline aromatization process in which gasoline was converted into BTX and $C_9+$ aromatic compounds. The composition of the feed which contained less than 880 ppm S is given in Table I. Not given in Table I are numerous components which were in very small quantities and, in some instances, whose chemical structures were unknown.

TABLE I

Composition of Feed

| Feed Component | Weight Percent |
|---|---|
| c-Hexene-2 | 1.104 |
| 1-Methyl-3-ethylbenzene | 2.254 |
| 1-Methyl-4-ethylbenzene | 1.057 |
| 1,3,5-Trimethylbenzene | 1.958 |
| 1-Methyl-2-ethylbenzene | 1.306 |
| 1,2,4-Trimethylbenzene | 9.977 |
| 1,2,3-Trimethylbenzene | 3.060 |
| 1-Methyl-3-I-propylbenzene | 0.286 |
| 2,3-Dihydroindene | 2.845 |
| 1,3-Diethylbenzene | 1.173 |
| 1-Methyl-3-n-propylbenzene | 1.543 |
| 1,4-Diethylbenzeneylbenzene | 0.910 |
| 1-Methyl-4-n-propylbenzene | 0.328 |
| n-Butylbenzene-ethylbenzene | 2.836 |
| 1-Methyl-2-n-propylbenzene | 0.889 |
| 1,4,-Dimethyl-2-ethylbenzene | 1.991 |
| s-C5-benzene/1,3-dimethyl-4-ethylbenzene | 2.958 |
| 1,2-Dimethyl-4-ethylbenzene | 3.454 |
| 1,2-Dimethyl-3-ethylbenzene | 1.007 |
| 1,2,4,5-Tetramethylbenzene | 1.936 |
| 1,2,3,5-Tetramethylbenzene | 2.695 |
| 5-Methylindan | 3.004 |
| 1-Ethyl-2-n-propylbenzene | 1.592 |
| 2-Methylindan | 3.040 |
| 1,3-Di-I-propylbenzene | 1.084 |
| Naphthalene | 4.767 |
| 2-Methylnaphthalene | 3.382 |
| 1-Methylnaphthalene | 1.184 |

A stainless-steel reactor tube (inner diameter 0.75 inch; length 20 inches) was filled with a 20 ml bottom layer of Alundum® alumina (inert, low surface area alumina), one of the catalysts (in 1/16 inch extrudates) in the center position 5 ml, and a 20 ml top layer of Alundum® alumina. The catalysts were pretreated with hydrogen (260 ml/minute) at 575° C. (starting at 25° C. then ramping at 10° C./min) for one hour. The feed was then introduced into the reactor at a rate of 20 milliliters/hour (WHSV=4.85–5.26), together with hydrogen gas at a rate of 260 ml of $H_2$/hours. The reaction temperature was 573° C. to 579° C. as shown in Table II, and the reaction pressure was 500 psig. The reactor effluent was cooled and analyzed with an on-line gas chromatograph at intervals of about 1 hour. The results are shown in Table II.

TABLE II

|  | Catalyst | | Reaction | | Reactor Effluent (wt %)[a] | | | |
|---|---|---|---|---|---|---|---|---|
| Catalyst | Incorp. Method[b] | Weight (g) | Temp (°C.) | Time (hr) | BTX | Xyl | Selct BTX | Conversion %[c] |
| Invention A | EDF | 3.59 | 572 | 7.46 | 35.5 | 21.0 | 0.69 | 51.8 |
| Control B | IMP | 3.55 | 574 | 6.47 | 22.4 | 15.4 | 0.62 | 36.1 |
| Control C | IMP | 3.27 | 578 | 7.49 | 16.1 | 11.8 | 0.60 | 26.8 |

[a]The values presented, except conversion, are weight percent. Xyl denotes the total weight % of all xylenes. Selct BTX is selectivity to BTX, calculated by dividing weight % BTX with % conversion.
[b]Incorporation method: IMP, incipient wetness impregnation with impregnating solution; EDF, invention process, equilibrium-deposition-filtration method.
[c]The % conversion was calculated as 100% − weight % $C_9$ + aromatic compound in effluent.

The results shown in Table II indicate that the invention catalyst A, which was promoted with Mo and Zn and was made by the invention process, had significantly higher yield of BTX and xylenes than control catalysts B (promoted with Mo and Zn, but made by conventional impregnation method) and control catalyst C (promoted with Mo and Zn, made by conventional impregnation method followed by steam treatment). The results also show that the invention catalyst had better selectivity to BTX than the control catalysts did.

The results clearly demonstrate that the present invention is well adapted to carry out the objects and attain the ends and advantages mentioned as well as those inherent therein. While modifications may be made by those skilled in the art, such modifications are encompassed within the spirit of the present invention as defined by the disclosure and the claims.

That which is claimed:

1. A process comprising contacting a $C_9$+ aromatic compound-containing fluid with a catalyst composition under a condition sufficient to effect the conversion of a $C_9$+ aromatic compound to a $C_6$ to $C_8$ aromatic hydrocarbon wherein said catalyst composition is prepared by the steps which comprise: (1) contacting an alumina with a molybdenum-containing compound and a zinc-containing compound in a liquid medium under a condition sufficient to incorporate said molybdenum-containing compound and zinc-containing compound into said alumina to form a modified alumina wherein the volume of said liquid medium is larger than the bulk volume of alumina; (2) removing the excess liquid medium containing the molybdenum-containing compound and zinc-containing compound; (3) drying said modified alumina; and (4) calcining said modified alumina under a condition sufficient to effect the conversion of said molybdenum-containing and zinc-containing compounds to their corresponding oxide form.

2. A process according to claim 1 wherein said $C_9$+ aromatic compound has the formula of $R_qAr$ wherein each R is a hydrocarbyl radical having 1 to about 15 carbon atoms and is independently selected from the group consisting of alkyl radicals, aryl radicals, alkaryl radicals, aralkyl radicals, alkenyl radicals, and combinations of any two or more thereof, q is a whole number from 1 to 5, and Ar is an aryl group.

3. A process according to claim 1 wherein said $C_9$+ aromatic compound comprises an aromatic hydrocarbon selected from the group consisting of 1,2,3-trimethylbenzene, 1,2,4-trimethylbenzene, 1,3,5-trimethylbenzene, 1,2,3,4-tetramethylbenzene, 1,2,3,5-tetramethylbenzene, 1,2,4,5-tetramethylbenzene, n-propylbenzene, 3-ethyltoluene, 4-ethyltoluene, 3-n-propyltoluene, 4-n-propyltoluene, 1,3-diethylbenzene, and combinations of any two or more thereof.

4. A process according to claim 1 wherein said $C_9$+ aromatic compound is derived from a paraffin aromatization process.

5. A process according to claim 4 wherein said paraffin is gasoline.

6. A process according to claim 1 wherein said contacting of said $C_9$+ aromatic compound-containing fluid with said composition is carried out in the presence of a hydrogen-containing fluid.

7. A process according to claim 6 wherein said process is carried out under a condition which comprises a liquid hourly space velocity of said fluid in the range of about 0.1 to about 30 g feed/g catalyst/hour, a gas hourly space velocity of said hydrogen-containing fluid in the range of about 10 ft³ gas/ft³ catalyst/hour to about 5,000 ft³/ft³ catalyst/hour, a molar ratio of hydrogen to said $C_9$+ aromatic compound in the range of about 0.5:1 to about 5:1, a pressure in the range of about 50 psig to about 750 psig, and a temperature in the range of about 250° C. to about 1000° C.

8. A process according to claim 7 wherein said condition comprises a pressure of about 200 to about 600 psig and a temperature of about 400° to about 650° C.

9. A process according to claim 8 wherein said $C_9$+ aromatic compound comprises an aromatic hydrocarbon selected from the group consisting of 1,2,3-trimethylbenzene, 1,2,4-trimethylbenzene, 1,3,5-trimethylbenzene, 1,2,3,4-tetramethylbenzene, 1,2,3,5-tetramethylbenzene, 1,2,4,5-tetramethylbenzene, n-propylbenzene, 3-ethyltoluene, 4-ethyltoluene, 3-n-propyltoluene, 4-n-propyltoluene, 1,3-diethylbenzene, and combinations of any two or more thereof.

10. A process according to claim 1 wherein said molybdenum-containing compound is selected from the group consisting of molybdenum(II) acetate, ammonium molybdate, ammonium dimolybdate, ammonium heptamolybdate, ammonium phosphomolybdate, molybdenum(III) bromide, molybdenum(II) chloride, molybdenum(IV) chloride, molybdenum(V) chloride, molybdenum hexacarbonyl, molybdenum(V) sulfide, sodium molybdate, potassium molybdate, molybdenum oxychloride, molybdenum fluoride, molybdenum(VI) tetrachloride oxide, ammonium tetrathiomolybdate, and combinations of any two or more thereof.

11. A process according to claim 1 wherein said molybdenum-containing compound is ammonium heptamolybdate.

12. A process according to claim 1 wherein said zinc-containing compound is selected from the group consisting of zinc acetate, zinc acetylacetonate, zinc arsenide, zinc bromide, zinc carbonate hydroxide, zinc chloride, zinc fluoride, zinc hydroxide, zinc iodide, zinc nitrate, zinc stearate, and combinations of any two or more thereof.

13. A process according to claim 10 wherein said zinc-containing compound is selected from the group consisting of zinc acetate, zinc acetylacetonate, zinc arsenide, zinc bromide, zinc carbonate hydroxide, zinc chloride, zinc fluoride, zinc hydroxide, zinc iodide, zinc nitrate, zinc stearate, and combinations of any two or more thereof.

14. A process according to claim 1 wherein said zinc containing compound is zinc nitrate.

15. A process according to claim 11 wherein said zinc containing compound is zinc nitrate.

16. A hydrodealkylation process comprising contacting, in the presence of a hydrogen-containing fluid, a fluid comprising a $C_9+$ aromatic compound with a catalyst composition under a condition sufficient to effect the conversion of said $C_9+$ aromatic compound to a $C_6$ to $C_8$ aromatic hydrocarbon wherein said catalyst composition is prepared by the steps comprising:

(1) contacting an alumina, which is calcined before being contacted, with both a molybdenum-containing compound and a zinc-containing compound in an aqueous solution under a condition sufficient to incorporate said molybdenum-containing compound and a zinc-containing compound into the alumina to form a modified alumina wherein the volume of said aqueous solution is larger than the bulk volume of said alumina; (2) without washing, removing the excess aqueous solution containing said molybdenum-containing compound and zinc-containing compound; (3) drying said modified alumina; and (4) calcining said modified alumina under a condition sufficient to effect the conversion of said molybdenum-containing compound and zinc-containing compound to their corresponding oxides wherein:

said $C_9+$ aromatic compound has the formula of $R_qAr$ wherein each R is a hydrocarbyl radical having 1 to about 15 carbon atoms and is independently selected from the group consisting of alkyl radicals, aryl radicals, alkaryl radicals, aralkyl radicals, alkenyl radicals, and combinations of any two or more thereof, q is a whole number from 1 to 5, and Ar is an aryl group;

said process is carried out under a condition which comprises a liquid hourly space velocity of said fluid in the range of about 0.1 to about 30 g feed/g catalyst/hour, a gas hourly space velocity of said hydrogen-containing fluid in the range of about 10 $ft^3$ gas/$ft^3$ catalyst/hour to about 5,000 $ft^3$/$ft^3$ catalyst/hour, a molar ratio of hydrogen to said $C_9+$ aromatic compound in the range of about 0.5:1 to about 5:1, a pressure in the range of about 50 psig to about 750 psig, and a temperature in the range of about 250° C. to about 1000° C.;

said molybdenum-containing compound is selected from the group consisting of molybdenum(II) acetate, ammonium molybdate, ammonium dimolybdate, ammonium heptamolybdate, ammonium phosphomolybdate, molybdenum(III) bromide, molybdenum(II) chloride, molybdenum (IV) chloride, molybdenum(V) chloride, molybdenum hexacarbonyl, molybdenum(V) sulfide, sodium molybdate, potassium molybdate, molybdenum oxychloride, molybdenum fluoride, molybdenum (VI) tetrachloride oxide, ammonium tetrathiomolybdate, and combinations of any two or more thereof; and said zinc-containing compound is selected from the group consisting of zinc acetate, zinc acetylacetonate, zinc arsenide, zinc bromide, zinc carbonate hydroxide, zinc chloride, zinc fluoride, zinc hydroxide, zinc iodide, zinc nitrate, zinc stearate, and combinations of any two or more thereof.

17. A process according to claim 16 wherein said $C_9+$ aromatic compound comprises an aromatic hydrocarbon selected from the group consisting of 1,2,3-trimethylbenzene, 1,2,4-trimethylbenzene, 1,3,5-trimethylbenzene, 1,2,3,4-tetramethylbenzene, 1,2,3,5-tetramethylbenzene, 1,2,4,5-tetramethylbenzene, n-propylbenzene, 3-ethyltoluene, 4-ethyltoluene, 3-n-propyltoluene, 4-n-propyltoluene, 1,3-diethylbenzene, and combinations of any two or more thereof; said condition comprises a pressure of about 200 to about 600 psig and a temperature of about 400° to about 650° C.; said molybdenum-containing compound is ammonium heptamolybdate; and said zinc-containing compound is zinc nitrate.

18. A process according to claim 17 wherein said $C_9+$ aromatic compound is derived from paraffin aromatization process.

19. A process according to claim 18 wherein said paraffin is gasoline.

20. A process comprising contacting a $C_9+$ aromatic compound-containing fluid, in the presence of hydrogen, with a catalyst composition under a condition sufficient to effect the conversion of said $C_9+$ aromatic compound to a $C_6$ to $C_8$ aromatic hydrocarbon wherein said catalyst composition is prepared by the steps which comprise: (1) contacting an alumina with a solution containing zinc nitrate and ammonium heptamolybdate under a condition sufficient to incorporate said zinc nitrate and ammonium heptamolybdate into said alumina to form a modified alumina wherein the volume of said liquid medium is larger than the bulk volume of alumina; (2) removing the excess solution; (3) drying said modified alumina; (4) calcining said modified alumina to produce a calcined modified alumina; and thereafter (5) treating said calcined modified alumina with a reducing agent to produce a zinc- and molybdenum-incorporated alumina; and said process is carried out under a condition which comprises a liquid hourly space velocity of said fluid in the range of about 0.1 to about 30 g feed/g catalyst/hour, a gas hourly space velocity of said hydrogen-containing fluid in the range of about 10 $ft^3$ gas/$ft^3$ catalyst/hour to about 5,000 $ft^3$/$ft^3$ catalyst/hour, a molar ratio of hydrogen to said $C_9+$ aromatic compound in the range of about 0.5:1 to about 5:1, a pressure in the range of about 50 psig to about 750 psig, and a temperature in the range of about 250° C. to about 1000° C.

21. A process according to claim 20 wherein said alumina is γ-alumina; said reducing agent is hydrogen; and said condition comprises a pressure of about 200 to about 600 psig and a temperature of about 400 to about 650° C.

22. A process according to claim 1 wherein said condition in step (1) further comprises a period in the range of from about 1 to about 150 hours.

* * * * *